(12) United States Patent
Lunenfeld

(10) Patent No.: US 6,492,177 B1
(45) Date of Patent: Dec. 10, 2002

(54) KIT FOR USE IN TREATMENT OF POLYCYSTIC OVARIAN DISEASE

(75) Inventor: Bruno Lunenfeld, Tel-Aviv (IL)

(73) Assignee: Applied Research Systems ARS Holding NV

(*) Notice: Subject to any disclaimer, the term of this patent is extended or adjusted under 35 U.S.C. 154(b) by 0 days.

(21) Appl. No.: 08/436,023

(22) Filed: May 5, 1995

Related U.S. Application Data

(60) Division of application No. 08/197,501, filed on Feb. 16, 1994, which is a continuation-in-part of application No. 07/807,847, filed as application No. PCT/EP91/00479 on Mar. 14, 1991, now abandoned.

(30) Foreign Application Priority Data

Mar. 16, 1990 (GB) ............................................... 9005958
May 25, 1990 (GB) ............................................... 9011823

(51) Int. Cl.⁷ ..................... G01N 33/53; C07K 14/575; C07K 14/59; A61K 38/22
(52) U.S. Cl. ............................ 435/975; 514/2; 514/15; 514/21; 530/313
(58) Field of Search ................................. 514/2, 15, 21; 530/313; 435/975

(56) References Cited

U.S. PATENT DOCUMENTS 4,845,077 A * 7/1989 Hodgen ......................... 514/2
5,130,137 A * 7/1992 Crowley, Jr. ................. 424/422

FOREIGN PATENT DOCUMENTS

EP 472 725 B1 * 3/1992
WO 91/14704 * 10/1991

OTHER PUBLICATIONS

Loz et al., *Endocrinal. Metab. Clin. N. America,* vol. 17, pp. 785–813, 1988.*
Coutts et al., Excertpa–Medica Int'l Congress Series, 652; 608 (1984).

* cited by examiner

Primary Examiner—Gary L. Kunz
Assistant Examiner—Stephen Gucker
(74) Attorney, Agent, or Firm—Dickstein, Shapiro, Morin & Oshinsky, LLP.

(57) ABSTRACT

Agents which increase the levels of human insulin-like growth factor-1 binding protein (h-ICFBP-1), such as an estrogen, are used in conjunction with a gonadotropin releasing hormone (GnRH) analogue in the treatment of PCOD and associated infertility.

7 Claims, No Drawings

KIT FOR USE IN TREATMENT OF POLYCYSTIC OVARIAN DISEASE

This is a division of application Ser. No. 08/197,501 filed Feb. 16, 1994, which is a continuation-in-part of Ser. No. 07/807,847 dated Jan. 14, 1992 (now abandoned) which was derived as a 371 from PCT/EP91/00479 filed on Mar. 14, 1991.

BACKGROUND OF THE INVENTION

1. Field of the Invention

The present invention relates to the treatment of polycystic ovarian disease (PCOD), and in particular a treatment for infertility associated therewith.

2. Related Prior Art

PCOD is a complex syndrome comprising a disorder of multiple etiologies involving a vicious circle of imbalance between various interdependent endocrine and peripheral structures. The syndrome is characterised by a variety of symptoms, some or all of which may be present in any one individual. These include menstrual abnormalities, hyperandrogenism, infertility and bilateral polycystic ovaries. Observations on the levels as well as the secretion and metabolism of the sex hormones helps to identify the pathophysiology of the syndrome.

Recently, several reports appeared showing that polycystic ovary diseases may be connected with acanthosis nigricans and insulin resistance. (For instance see: Kahn C R, Flier J S, Bar R S, Archer J A, Gordon P, Martin M M, Roth J: "The syndrome of insulin resistance and acanthosis nigricans. Insulin-receptor disorders in man." New Engl J Med 294:739, 1976; Burghen G A, Givens J R, Kitabachi A E: "Correlation of hyperandrogenism with hyperinsulinism in polycystic ovarian disease." J. Clin. Endorinol. Metab. 50:113, 1980; and Shapiro A G: (1981). "Pituitary adenoma, menstrual disturbance, hirsutism and abnormal glucose tolerance." Fertil Steril 35: 226, 1981.) This indicates clearly that PCOD may be linked with insulin action and its control.

It also became apparent that growth factors (GF) play a modulating role in the ovarian response to gonadotropic stimulation as described by Adashi E A, Resnick C E, Svoboda M E, van Wyk J J: "Somatomedin C enhances induction of LH receptors by FSH in cultured rat granulosa cells." Endrocrinol. 116:2369, 1988. Homburg et al ("Growth hormone facilitates ovulation induction by gonadotropins," Clin. Endocrinol. 29:113, 1988) demonstrated that the addition of growth hormone (hGH) to menopausal gonadotropin (hMG) therapy reduced the amount of gonadotropins required for ovulation induction. Blumenfeld & Lunenfeld ("The potentiating effect of growth hormone on follicle stimulation with human menopausal gonadotropins in a panhypopituitary patient". Fertil. Steril. 25:238, 1989) demonstrated that patients with panhypopituitarism require excessive amounts of gonadotropins which can be reduced by concomitant administration of growth hormone. Menashe et al ("Does endogenous hormone reserve correlate to ovarian response to menopausal gonadotropins?" Isr. J. Med. Sci. 25:296, 1889) showed that anovulatory women with reduced growth hormone reserve (as established by the clonidine growth hormone reserve test) needed significantly more gonadotropins to induce follicular maturation and ovulation than women who were clonidine positive.

Urdl, in "Polycystic ovarian disease: Endocrinological parameters with specific reference to growth hormone and somatomedin-C." Arch. Gynecol. Obstet. 243:13, 1988, studied 33 women with polycystic ovarian disease and in 18 of them observed decreased hGH levels and increased Somatomedin-C (Sm-C) values. Pekonen et al in "Decreased 34K insulin-like growth factor binding protein in polycystic ovarian disease". Fertil. Seteril. 51:972, 1989, found that patients with PCOD had decreased levels of human insulin-like growth factor-1 binding protein (hIGFBP-1).

All these observations indicate definitely that growth hormone and other growth factors as well as their binding proteins may play an important role in pathophysiology of PCOD.

Growth hormone (GH) stimulates the systemic release of insulin-like growth factor-1 (ICF-1) from the liver. GH and probably other growth factors binding protein is also produced by the liver. Moreover, Leung and co-workers in "Growth hormone receptor and serum binding protein: purification, cloning and expression." Nature 330:537, 1987, showed that the growth hormone receptor from rabbit liver and the growth hormone binding protein from rabbit serum having the same amino-terminal amino-acid sequence indicating that the binding protein corresponds to the extracellular hormone-binding domain of the liver receptor. It is becoming clear that the liver must play an important role in both normal and abnormal function of the ovaries.

At this stage the inventor believes that PCOD is connected with higher levels of free IGF-1 (Somatomedin C). Since Somatomedin C increases the ovarian response to gonadotropins, this may explain the excessive production of androgens by the luteinising hormone (LH) responsive structural ovarian components. Furthermore, it also explains the hyper-responsiveness of the ovarian follicular elements to follicle stimulating hormone (FSH) stimulation. If so, one pathophysiological basis of the PCOD could be explained as follows: the increased levels of free IGF-1 result in excessive follicular stimulation on the one hand and in overproduction of androgens leading to follicular atresia on the other hand.

PCOD has been treated by several schemes. Since the syndrome is associated with increased levels of androgen, one treatment is to remove a section of androgen-producing tissue (ovarian wedge vesection) but this has now been replaced wherever possible by hormonal therapy. Administration of glucocorticoid reduces excessive androgen production mostly of adrenal origin and has been used with relative success in the management of PCOD treatment originating from adrenal disease. Antiestrogens such as clomiphene citrate have also been used. Luteinising hormone releasing hormone analgoue has been shown to suppress PCOD by Chang et al in J. Chem. Endomet. Metab. 56:897 (1983).

Woodruff et al in U.S. Pat. No. 5,102,868 propose to treat PCOD by inhibiting maturation of follicles by administering activin to the ovary of a female PCOD sufferer. The activin composition is administered directly to the ovary or the immediate surrounding area. Activin is a member of family of growth and differentiation factors which includes also transforming growth factors and is a dimer of inhibin β subunits. It has been shown to have follicle stimulating hormone releasing activity, suppresses androgen production, and inhibits progesterone production. Its activity in showing the rate of follicular maturation of PCOD patients is due to its activity as an intragonadal down-regulator of reproductive function.

Human menopausal gonadotropin (hMG) (eg a 50:50 mixture in I.U. of follicle stimulating hormone (FSH) and luteinising hormone (LH)) and urofollitrophin (FSH substantially free of LH) have been used to treat infertile PCOD patients. Urofollitrophin may be preferred as these patients are prone to hyperstimulation by LH. All gonadotropin therapy is subject to the risk of ovulation of multiple follicles and hyperstimulation. It has also been proposed to suppress endogenous secretion of gonadotropins by administration of a gonadotropin releasing hormone (GnRH) analogue prior to administration of exogenous gonadotropins and this does have some benefits as described by Coutts et al in Exerpta-Media Int. Congress Series 652:608, 1984.

However since hIGFBP-1 and the level of free or bond IGF-1 are not affected by GnRH analogues, it is also logical that in this group of PCOD patients, the basic ovarian response to hMG or hFSH (urofollitrophin) stimulation is not significantly changed by pituitary down regulation.

It has been proposed to use as a contraceptive regimen the administration of luteinising hormone releasing hormone (LHRH) analogues as these have been found to block ovulation. Crowley in U.S. Pat. No. 4,762,771 discloses that LHRH analgoue administration alone leads to side effects of estrogen deficiency and proposes overcoming these by administering estrogen simultaneously with the LHRH analogue and, in a latter stage of the menstrual cycle, adding also a progestrational steroid. The method is designed to inhibit ovulation.

SUMMARY OF THE INVENTION

According to the present invention there is provided method of treating PCOD in which a gonadotropin releasing hormone analogue and a human insulin-like growth factor-1 binding agent increasing agent are administered to a woman in need of such treatment.

In the method, the human insulin-like growth factor-1 binding agent (hIGFBP-1) increasing agent is preferably an estrogen.

The primary use of the method of treatment with which the present invention is concerned is in the treatment of infertility associated with PCOD. The method therefore usually includes induction of ovulation by using gonadotropins in the usual way. The induction of ovulation thus usually involves follicular maturation which is induced by the administration of human menopausal gonadotropins (hMC) (eg a 50:50 mixture in I.U. of follicle stimulating hormone (FSH) and luteinising hormone (LH)) or of urofollitrophin (FSH substantially free of LH), followed by ovulation induction itself by human chorionic gonadotropin (hCG).

The administration of estrogen increases the level of IGF-1 binding globulin, thus diminishing the excess of free IGF-1 available to the growing follicles. This has the consequence that the response of the ovaries to exogenous stimulation by gonadotropins will be improved and will be more reliable. Estrogen administration alone, in particular at high dose, would lead to an hormonal environment changing pituitary sensitivity so as to result in the release of excessive LH and this untimely release of LH would lead to anovulation. The administration of the gonadotropin releasing hormone (GnRH) analogues prevents the secretion of endogenous LH and FHS. Follicular development and ovulation are then induced in the normal way following the pituitary down regulation of GnRH analogue, by administration of exogenous hMG or urofollitrophin and then hCC.

DETAILED DESCRIPTION OF THE INVENTION

In the invention, the GnRH analgoue may be an agonist or an antagonist of GnRH. In general, if it is an agonist then it is generally administered in a first cycle with estrogen and the gonadotropin administered in the following cycle. This allows the inhibitory action of the agonist to work. Where the analogue is an antagonist, then it may also be administered in a first cycle with the other components being administered in a succeeding cycle, but can also be administered co-jointly, that is over the same period as the other components.

Gonadotropin releasing hormone analogues are well known in the art. The naturally occurring hormone is a decapeptide having the following structure:

p-Glu-His-Trp-Ser-Tyr-Gly-Leu-Arg-Pro-Gly-NH$_2$.

Many agonists and antagonists have been synthesized. As agonist is a physiologically active peptide which enhances the biological activity of GnRH itself whereas an antagonist inhibits that activity. The biological activity of GnRH is the stimulation of the release of luteinising hormone (LH) and follicle stimulating hormone (FSH) from the anterior pituitary gland, and thereby the control of the reproductive cycle in mammals.

Typical GnRH antagonists are described in Rees et al, J.Med. Cheml. 17, 1016 (1974), Coy et al, Peptides 1976 (Loffed Ed., Editions de L'Universite de Bruxelle 1977) p.463, Beattie et al, J.Med. Chem., 18, 1247 (1975), Channabasavaiah et al, Biochem. Biophys. Res. Commun., 86, 1266 (1979) and U.S. Pat. Nos. 4,317,815 and 4,431,635, and include [Ac-pCl-Phe$^1$, pCl-Phe$^2$, D-Trp$^3$, D-Arg$^6$, D-Ala$^{10}$] GnRH Hcl, [D-Phe$^2$]-LHRH, [D-Phe$^2$, D-Phe$^6$]-LHRH, [D-Phe$^2$, Phe$^3$, D-Phe$^6$]-LHRH, [D-Phe$^2$, D-Trp$^3$, D-Phe$^6$]-LHRH, [D-p-F-Phe-D-Ala$^6$]-LHRH, and [Ac-D-Phe$^1$, D-Phe$^2$, D-Trp$^{3,6}$]-LHRH.

The GnRH antagonist is administered in an amount which is sufficient to suppress endogeneous gonadotropin secretion. In general, the average daily dosage will be in the range of about 1.0–3.0 mg per kg and preferably in the range of about 1.5–2.5 mg/kg. The suitable dosage can be determined by monitoring FSH and LH levels after administration of the antagonist.

GnRH agonists are also known. One example is D-Ser (TBU)$^6$-EA$^{10}$-LHRH (Hoe 766) (buserelin, EA is des-Gly-NH$_2$10-ethylamide) and another is sold under the name Decapeptyl by CR which is D-Trp$^4$-LHRH. Others are D-Trp$^6$-EA$^{10}$-LHRH, D(NAL$_2$)$^6$-LHRH (Naferelin), and D-His(imBBzl)$^6$-(Pro-NEt)$^9$-LHRH. The agonist is administered in an amount such that LH and FSH secretion is suppressed, which again can be monitored using routine techniques.

In the invention, the estrogen that is used is preferably an estradiol or a derivative thereof. A suitable derivative is estradiol benzoate. In general the estrogen is used in an effective amount for increasing IGF-1 binding globulin and thereby to decrease the amount of free IGF-1. The work of Urdl, cited above, suggests that the estrogen should be administered in relatively high doses, eg a daily dose (intramuscular) of 1 mg.

The administration of estrogen and GnRH analogue create a hormonal and intrafollicular environment favourable for normal response to induction of ovulation with hMG or urofollitrophin followed by hCG. The induction of ovulation is carried out in the manner described in EP-A-016103, for instance the amount of gonadotropins used will generally be the same as in that reference.

The compositions in which the various active ingredients are supplied may be presented in the conventional forms for systemic administration, that is for oral, nasal or, preferably, parenteral administration, generally intramuscular administration. The various active ingredients, may be provided in the same composition, where they can be administered at the same time, although usually are presented in separate compositions, which are thus suitable for co-joint use or for use over different periods.

The invention may be used for in vitro or in vivo fertilisation.

The following example outlines the regimen to be used for the method of treatment with which the present invention is concerned.

EXAMPLE

The following is a protocol by which the present invention will be assessed. In a method of treatment, it is likely that some or all of the blood assays will not be carried out. The Clonidine test is likely to be carried out and will thus involve some or all of the blood assays. However, it is unlikely that it will be necessary to carry out the blood assays during the second cycle during administration of the estrodiol benzoate. Since the administration of FSH may be individually controlled and monitored the blood assays during that period may be carried out during the treatment itself.

The protocol is as follows:

Cycle 1

At the beginning of the preceding cycle a Clonidine test will be performed (2 clonidine. HCl tablets of 0.150 mg) are administered orally.

Blood will be drawn and assayed for: FSH, LH, growth hormone (GH), estradiol (E-2), IGF-1, PRL at time 0=before administration of Clonidine, and 30, 60, 90 and 120 min. following the administration of Clonidine GH will be measured. All these blood samples will be saved for future assays of IGF-1 and sex binding globulins. At the same day US scan of the ovaries will be performed.

GnRH analogue (Decapeptyl CR 3.2 mg) will be injected i.m on day 7th or 8th of the luteal phase of the cycle. Prior to the injection, a beta-hCG test will be performed in order to exclude early pregnancy.

Cycle 2

On day 4 a US scan of the ovaries will be performed and blood will be drawn for: E-2, FSH, LH, GH, IGG-1 (possibly also for IGF-1 and sex binding globulins).

On day 4 1 mg of Estradiol Benzoate will be injected i.m.

On day 7 E-2, FSH, LH will be assayed.

On the same day 1 mg of Estradiol Benzoate will be injection i.m.

On day 10 E-2, FSH, LH, GH, IGF-1 (possibly also IGF-1 and sex binding globulins) will be assayed.

On the same day urofollitrophin, i.e. FSH (Metrodin, Teva-Serono) 150 IU will be administered i.m. and the treatment will be continued according to the individually adjusted dose and monitored by daily E-2, FSH, LH assays and US scans.

If on day 16, ie after 6 days of Metrodin therapy, no follicles greater than 17 mm and/or E-2 levels will not reach 350 pg/ml, Metrodin will be continued together with daily injections of Decapeptyl 0.1 mg i.m. until induction of ovulation will be possible. Ovulation will be induced by i.m. injection of 10,000 IU of hCG administered 24 h. after the final agonist dose. A US scan of the ovaries will be performed and blood will be taken for E-2, FSH, LH, GH IGF-1 (possibly also IGF-1 and sex binding globulins).

In cases subjected to IVF, the above tests will be repeated on the day of ovum pick up and follicular fluid will be assayed for E-2, IGF-1 (possibly also IGF-1 and sex binding globulins).

What is claimed is:

1. A kit containing an estrogen composition and a gonadotropin releasing hormone analogue composition in separate containers for separate co-joint administration to a woman for the treatment of polycystic ovarian disease, said kit containing also gonadotropin composition in which the gonadotropin is selected from the group consisting of human menopausal gonadotropins and urofollitrophin.

2. Kit according to claim 1 containing also gonadotropin composition in which the gonadotropin is selected from the group consisting of human menopausal gonadotropins and urofollitrophin.

3. Kit according to claim 1 in which each said composition is suitable for intramuscular injection.

4. A kit according to claim 1 wherein the gonadotropin releasing hormone analog in an antagonist.

5. Kit according to claim 4 in which the antagonist is selected from the group consisting of [Ac-pCl-Phe$^1$, pCl-Phe$^2$, D-Trp$^3$, D-Arg$^6$, D-Ala$^{10}$] GnRH HCl, [D-Phe$^2$]-LHRH, [D-Phe$^2$, D-Phe$^6$]-LHRH, [D-Phe$^2$, Phe$^3$, D-Phe$^6$]-LHRH, [D-Phe$^2$, D-Trp$^3$, D-Phe$^6$]-LHRH, [D-p-F-Phe-D-Ala$^6$]-LHRH, and [Ac-D-Phe$^1$, D-Phe$^2$, D-Trp$^{3,6}$]-LHRH.

6. A kit according to claim 1 wherein the gonadotropin releasing hormone analog is an agonist.

7. Kit according to claim 6 in which the said agonist is selected from the group consisting of D-Ser (TBU)$^5$EA$^{10}$-LHRH and Decapeptyl.

\* \* \* \* \*